United States Patent
Hartung et al.

(10) Patent No.: US 8,148,430 B2
(45) Date of Patent: Apr. 3, 2012

(54) PROCESS FOR THE HYDROGENATION OF AROMATIC COMPOUNDS

(75) Inventors: Rolf Hartung, Neuberg (DE); Franz Hitzel-Zerrahn, Mörfelden (DE); Thomas Müller, Bruchköbel (DE); Jörg Pietsch, Alzenau (DE)

(73) Assignee: Evonik Degussa GmbH, Essen (DE)

( * ) Notice: Subject to any disclaimer, the term of this patent is extended or adjusted under 35 U.S.C. 154(b) by 1208 days.

(21) Appl. No.: 10/565,366

(22) PCT Filed: Jun. 19, 2004

(86) PCT No.: PCT/EP2004/006654
§ 371 (c)(1),
(2), (4) Date: Jan. 23, 2006

(87) PCT Pub. No.: WO2005/014526
PCT Pub. Date: Feb. 17, 2005

(65) Prior Publication Data
US 2006/0205954 A1  Sep. 14, 2006

(30) Foreign Application Priority Data
Jul. 24, 2003  (DE) .................................. 103 33 588

(51) Int. Cl.
*A61K 31/135* (2006.01)
(52) U.S. Cl. ..................................... 514/646
(58) Field of Classification Search .................. 514/646
See application file for complete search history.

(56) References Cited

U.S. PATENT DOCUMENTS

| | | | |
|---|---|---|---|
| 4,788,322 A | 11/1988 | Schuda et al. | |
| 5,039,649 A | 8/1991 | Lippert et al. | |
| 6,316,381 B1 | 11/2001 | Auer et al. | |

FOREIGN PATENT DOCUMENTS

| | | |
|---|---|---|
| EP | 0 427 939 | 5/1991 |
| EP | 0 438 311 | 7/1991 |
| EP | 0 823 416 | 8/1996 |
| WO | WO 91/07430 | 5/1991 |

OTHER PUBLICATIONS

International Search Report for PCT/EP2004/006654 filed Jun. 19, 2004.
International Preliminary Report on Patentability for PCT/EP2004/006654 filed Jun. 19, 2004.
Alexander, et al., "A Diastereoselective Synthesis of (2S, 3R, 4S)-2-Amino-1-cyclohexyl-6-methylheptane-3,4-diol, The Abbott Aminodiol," *Tetrahedron Letters* 37:1961-1964 (1996).
Birch, et al., "The Structure and Some Reactions of the Iron Tricarbonyl Complex of Thebaine," *J. Chem. Soc. C*. 531 (1968).
Bláha, et al., "Stereoisomeric Chiral 2,9-Diazabicyclo[4.4.0]Decane-3-,10-Diones as Models of Dipeptide Grouping: Synthesis, X-Ray, IR, NMR, and CD Studies," *Coll. Czech. Chem. Commun.* 49:712-742 (1984).
Clingman, et al., "Effect of Amines on Hydrogenolysis of Alkylphenols," *J. Org. Chem.* 23:276-280 (Feb. 1958).
Corringer, et al., "CCK-B Agonist of Antagonist Activities of Structurally Hindered and Peptidase-Resistant Boc-CCK$_4$ Derivatives," *J. Med. Chem.* 36:166-172 (1993).
Devant, et al., "Steroselektive Aldolreaktion Mit Chiralen Sekundären Acetamiden," *Chem. Ber.* 119:2191-2207 (1986).
Eisler, et al., "Amino Acids and Peptides. LXV. Analogues of Oxytocin," *Coll. Czech. Chem. Commun.* 31:4563-4580 (1966).
Faustini, et al., "Stereospecificity in the Transformation of α-Aminoacids into Fluroracids," *Tetrahedron Letters* 22:4533-4536 (1981).
Hayashi, et al., "Chiral (β-Aminoalkyl)Phosphines. Highly Efficient Phosphine Ligands for Catalytic Asymmetric Grignard Cross-Coupling," *J. Org. Chem.* 48:2195-2202 (1983).
Harris, et al., "Structure of Ristocetin A: Configurational Studies of the Peptide," *J. Am. Chem. Soc.* 104: 363-365 (1982).
Hoekstra, et al., "Large-Scale Synthesis of Anticoagulant Decapeptide MDL 28050," *Tetrahedron* 48:307-318 (1992).
Ishida, et al., "Micropeptins 88-A to 88-F, Chymotrypsin Inhibitors from the Cyanobacterium *Microcystis aeruginosa* (NIES-88)," *Tetrahedron* 54: 5545-5556 (1998).
Minnaard, et al., "Synthesis of Enantiomerically Pure Cyclohexylglycine," *Synthetic Communications* 29(24): 4327-4332 (1999).
Plata, et al., "The Stereospecific Preparation of an Hydroxyethylene Isotere Precursor via a Novel Piperidine-2,5-Dione Template," *Tetrahedron Letters* 32(30): 3623-3626 (1991).
Schuda, et al., "A Short and Efficient Synthesis of (3S, 4S)-4-[(*tert*-Butyloxycarbonyl)amino]-5-cyclohexyl-3-hydroxypentanoic Acid Ethyl Ester," *J. Org. Chem.* 53: 873-875 (1988).
Tamura, et al., "Guanylpiperidine Peptidomimetics: Potent and Selective bis-Cation Inhibitors of Factor Xa," *Bioorg. Med. Chem. Lett.* 10(8): 745-749 (Apr. 2000).
Tamura, et al., "A Synthesis of Optically Active α-Cyclohexylglycine," *Synthetic Communications* 8(5): 345-351 (1978).
Denmark, et al., "Asymmetric Construction of Quaternary Centers by Enantioselective Allylation: Application to the Synthesis of the Serotonin Antagonist LY426965," *Organic Letters* 4(11):1951-1953 (2002).

*Primary Examiner* — Shawquia Young
(74) *Attorney, Agent, or Firm* — Law Office of: Michael A. Sanzo, LLC

(57) ABSTRACT

The present invention focuses on a process for the hydrogenation of aromatic or heteroaromatic compounds and in particular on the ring hydrogenation of compounds having the formula (I).

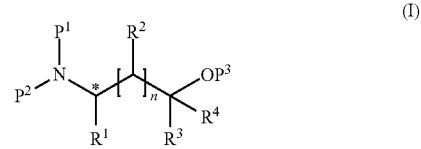

Aromatic amino acids and amino alcohols can be successfully ring-hydrogenated using a platinum-rhodium mixed catalyst. The products can be used inter alia as mimetics in bioactive peptide active ingredients.

20 Claims, No Drawings

PROCESS FOR THE HYDROGENATION OF AROMATIC COMPOUNDS

CROSS REFERENCE TO RELATED APPLICATIONS

The present application represents U.S. national stage of international application PCT/EP2004/006654, which has an international filing date of Jun. 19, 2004, and which was published in English under PCT Article 21(2) on Feb. 17, 2005. The international application claims priority to German application 103 33 588.9, filed on Jul. 24, 2003. These prior applications are hereby incorporated by reference in their entirety.

FIELD OF THE INVENTION

The present invention concerns a process for the hydrogenation of aromatic or heteroaromatic compounds. In particular, the invention concerns the hydrogenation of aromatic compounds such as (I)

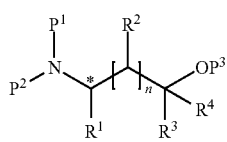

in the presence of a platinum-rhodium mixed catalyst.

BACKGROUND OF THE INVENTION

The hydrogenation of aromatic compounds is a standard reaction in organic chemistry and the resulting products are utilised commercially in many products.

Ring-hydrogenated amino acids and derivatives thereof, as structural mimetics of the natural amino acids valine and isoleucine, are interesting building blocks in peptide chemistry, for example (J. Med. Chem. 1993, 36, 166; Coll. Czech. Chem. Commun. 1984, 49, 712; Coll. Czech. Chem. Commun. 1966, 31, 4563; Synthetic Communications, 1978, 8, 345), and are used in a number of active ingredients, particularly renin inhibitors (e.g. WO 91/07430, EP 438311 and EP 427939) and thrombin inhibitors (e.g. melagatran and ximelagatran, Drugs of the Future 2001, 26, 1155). There is therefore a corresponding level of interest in the economical production of such amino acids on an industrial scale.

One possibility for the production of these compounds is the hydrogenation of corresponding aromatic precursors, many of which are available at a reasonable cost in enantiopure form (e.g. phenylalanine, phenylglycine and tyrosine). However, although the hydrogenation of simple, unsubstituted aromatic hydrocarbons to the corresponding saturated compounds under pressure in the presence of a noble metal catalyst is relatively straightforward, the hydrogenation of substituted aromatics is substantially more difficult. Secondary reactions can occur, such as e.g. a hydrogenolytic cleaving of substituents, particularly if palladium and platinum catalysts are used (Synthetic Communications, 1999, 29, 4327). Detailed investigations of the reactions are therefore necessary in many of these cases in order to optimise the reaction conditions (J. Org. Chem., 1958, 23, 276; Org. Syn., 1947, 27, 21).

An additional problem occurs if the substituent is carrying an asymmetrical C atom (particularly if it is in the benzyl position), since there is always a danger of partial racemisation (Synthetic Communications, 1978, 8, 345; EP 0823416). The racemisation-free hydrogenation of e.g. phenylglycine to cyclohexylglycine is therefore an especially critical reaction.

Several processes for the hydrogenation of phenylglycine, phenylalanine and other amino acids having aromatic substituents are described in the literature. Palladium, $PtO_2$ (Adam's catalyst), platinum, ruthenium and rhodium were used therein as catalysts.

However, as a consequence of the hydrogenolytic cleaving of the benzyl amino group that occurs as a secondary reaction, the hydrogenation of phenylglycine with $Pd(OH)_2$ (Synthetic Communications, 1978, 8, 345) generates only moderate yields. In addition, the cyclohexylglycine produced in this way was partially racemised.

The use of $PtO_2$ as a hydrogenating catalyst is described in a large number of publications. However, in most cases (U.S. Pat. No. 4,788,322; J. Org. Chem., 1988, 53, 873; TH 1992, 48, 307; THL 1996, 37, 1961; TH 1998, 54, 5545) only phenylalanine was hydrogenated, so no conclusion can be drawn about racemisation in the benzyl position. In two cases phenylglycine is also described as an educt (J. Am. Chem. Soc., 1982, 104, 363; Chem. Berichte 1986, 119, 2191). In the second case at least, a partial racemisation of the product is probable because of the specified angle of rotation. Other disadvantages of this method are the relatively long hydrogenation times (18 h) and the use of acetic acid as solvent, since this makes it more difficult to isolate the products.

Platinum itself has also been used as a catalyst (J. Chem. Soc. C, 1968, 531; THL, 1991, 32, 3623), although only the hydrogenation of phenylalanine is described in these cases, so again no conclusion can be drawn about a possible racemisation. In addition, no details are given of yields or of the pressures, reaction temperature and reaction times required. On the basis of the details given in Synthetic Communications, 1999, 29, 4332, however, it must be assumed that these hydrogenation reactions do not proceed particularly advantageously.

Patent EP 0823416 describes the use of a ruthenium catalyst for the hydrogenation of phenylglycine and phenylalanine, although at 65% the yields are moderate and unacceptable on an industrial scale.

Finally, rhodium catalysts have also been used for the hydrogenation of phenylglycine (Synthetic Communications, 1999, 29, 4327). In this case, however, the hydrogenation times (40 h) are very long, despite the use of more than 10 wt. % catalyst. Furthermore, a major disadvantage of the pure rhodium catalyst described here (5% Rh/C) is the high price of rhodium, which is by far the most expensive of the noble metals mentioned here.

DESCRIPTION OF THE INVENTION

The object of the present invention was therefore to provide details of another process for the hydrogenation of aromatic radicals of compounds having formula (I), which helps to prevent the aforementioned disadvantages of the prior art processes, particularly with regard to yield and risk of racemisation. This process should moreover also be able to be used on an industrial scale, i.e. it should be particularly advantageous from both an economic and an ecological perspective.

Quite surprisingly, but no less advantageously for that, the stated objects are achieved particularly simply according to the invention in that in a process for the hydrogenation of aliphatic-substituted aromatic or heteroaromatic compounds having an asymmetrical C atom, hydrogenation is performed in the presence of a platinum-rhodium mixed catalyst. When used according to the invention the proposed catalyst material leads to an almost completely racemisation-free hydrogenation product. With figures in some cases well above 94%, the yields are at the upper end of what is technically feasible. This shows that the formation of secondary products is inhibited correspondingly. A further advantage can be seen in the fact that the actual hydrogenation is completed in extremely short times of around 6 to 8 hours, which advantageously helps to raise the space-time yield, which is especially critical on an industrial scale. Aromatic or heteroaromatic compounds displaying the asymmetrical site in the benzyl position are preferred.

In a second aspect the invention relates in particular to a process for the hydrogenation of the aromatic nucleus of compounds having the general formula (I)

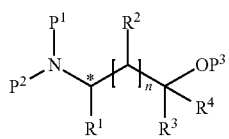

(I)

wherein n can be 0, 1, 2

$R^1$ represents unsubstituted or substituted ($C_6$-$C_{18}$) aryl, ($C_7$-$C_{19}$) aralkyl, (($C_1$-$C_8$) alkyl)$_{1-3}$ ($C_6$-$C_{18}$) aralkyl (($C_1$-$C_8$) alkyl)$_{1-3}$ ($C_6$-$C_{18}$) aryl, ($C_3$-$C_{18}$) heteroaryl, ($C_4$-$C_{19}$) heteroaralkyl, (($C_1$-$C_8$) alkyl)$_{1-3}$ ($C_3$-$C_{18}$) heteroaryl, $R^2$ denotes H, OH, ($C_1$-$C_8$) alkyl, ($C_2$-$C_8$) alkoxyalkyl, ($C_6$-$C_{18}$) aryl, ($C_7$-$C_{19}$) aralkyl, ($C_3$-$C_{18}$) heteroaryl, ($C_4$-$C_{19}$) heteroaralkyl, (($C_1$-$C_8$) alkyl)$_{1-3}$ ($C_6$-$C_{18}$) aryl, (($C_1$-$C_8$) alkyl)$_{1-3}$ ($C_3$-$C_{18}$) heteroaryl, ($C_3$-$C_8$) cycloalkyl, (($C_1$-$C_8$) alkyl)$_{1-3}$ ($C_3$-$C_8$) cycloalkyl, ($C_3$-$C_8$) cycloalkyl ($C_1$-$C_8$) alkyl, $R^3$ and $R^4$ together denote an $=$O function or H, ($C_1$-$C_8$) alkyl, ($C_6$-$C_{18}$) aryl, $P^1$ and $P^2$ mutually independently stand for hydrogen or an amino protective group or together stand for a bifunctional amino protective group, $P^3$ represents hydrogen or a hydroxyl protective group or carboxyl protective group and the C atom marked with * is an asymmetrical C atom, this hydrogenation being performed in the presence of a platinum-rhodium mixed catalyst. In the hydrogenation according to the invention the same advantages are found for the compounds claimed here as are described above. All natural and synthetic aromatic amino acids familiar to the person skilled in the art can be used according to the invention as educt, in particular α- and β-amino acids or the amino alcohols produced therefrom by reduction of the carboxyl function. Examples of natural amino acids can be found in Bayer-Walter Lehrbuch der organischen Chemie, 1991, S. Hirzel Verlag, 22$^{nd}$ edition, p. 822ff. Preferred synthetic amino acids are cited in DE19903268.

The amino acids can be used in the reaction in protected or unprotected form. Protective groups that are inert in respect of hydrogenation are preferred. A list of common amino acid protective groups is given in Green et al. (Greene, T. W., Protective Groups in Organic Synthesis, J. Wiley & Sons, 1981). Examples of amino protective groups that are preferably used are: acetyl, MoC, EOC, formyl, tert-butyl oxycarbonyl. Examples of carboxyl protective groups and hydroxyl protective groups can likewise be found in Green et al. They are in particular esters such as e.g. benzyl, tert-butyl, ethyl and methyl ester. In terms of the hydroxyl protective group, ethers such as tert-butyl, methyl, methoxymethyl or acyl protective groups such as formyl or acetyl are suitable. The protected derivatives of the aromatic amino acids can be produced from the free amino acids by simple means using standard methods (Houben-Weyl Volume XV/1, 1974, Georg Thieme Verlag).

Compounds having the general formula II

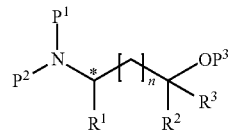

(II)

wherein n is 0, 1, $R^1$ represents unsubstituted or substituted ($C_6$-$C_{18}$) aryl, ($C_7$-$C_{19}$) aralkyl, (($C_1$-$C_8$) alkyl)$_{1-3}$ ($C_6$-$C_{18}$) aryl radicals, $R^2$ and $R^3$ are H or together are $=$O, $P^1$ and $P^2$ mutually independently stand for hydrogen or an amino protective group or together stand for a bifunctional amino protective group, $P^3$ represents hydrogen, a hydroxyl protective group or a carboxyl protective group and the C atom marked with * is an asymmetrical C atom, are preferably used in the reaction according to the invention. Examples thereof are L-phenylalanine, D-phenylalanine, L-phenylglycine, D-phenylglycine, L-tyrosine and D-tyrosine.

In principle the person skilled in the art is free to choose the relative composition of the hydrogenating catalyst. He or she will be guided here by operational results and by the costs of materials. The optimum composition can then be determined by routine experiments. A process in which a ratio of platinum to rhodium of between 20:1 and 1:1 (w/w) is used in the catalyst is preferred. The ratio is most particularly preferably 10:1 to 2:1, extremely preferably 5:1 to 3:1 (w/w).

The amount of catalyst to be used can be chosen freely by the person skilled in the art. In this case too, the aim should be to optimise the reaction in terms of economic perspectives. The catalyst is preferably used in a quantity of 0.1 to 20 wt. %, relative to the compound to be hydrogenated. The quantity is most preferably 1 to 15 wt. %, extremely preferably between 2 and 10 wt. %.

The catalyst is advantageously used in the supported state. This means that the catalyst is adsorbed on a support. All compounds used by the person skilled in the art for this purpose can serve as support materials. A list of suitable materials can be found in Ullmann's Encyclopedia of Industrial Chemistry, Volume A5, VCH, 1986, p. 347ff and in literature cited therein, and in Houben-Weyl, Methoden der Organischen Chemie, Volume 4/2, p. 146 ff. Of these, activated carbon and aluminium oxide should be emphasised in particular.

The platinum-rhodium catalysts that are used can contain between 1 and 10 wt. % noble metal (relative to the support), 4 to 6 wt. % being particularly preferred.

The hydrogenation according to the invention can be performed in solvents used for this purpose by the person skilled in the art. These are in particular those that are inert in respect of hydrogenation and that dissolve both educts and products to an adequate extent. The hydrogenation is preferably performed in the presence of solvents selected from the group comprising water, alcohols, ethers or mixtures thereof. In the hydrogenation of unprotected or only amino-protected or only hydroxyl/carboxyl-protected aromatic amino acids, it can be advantageous to add at least 1 equivalent of a base (for unprotected or only N-protected amino acids) or 1 equivalent of an acid (for unprotected or only hydroxyl/carboxyl-protected amino acids). Examples of bases that can be used here are NaOH, KOH, $NH_3$ or amine bases such as triethylamine. Examples of acids are HCl, $H_2SO_4$, $H_3PO_4$, acetic acid and trifluoroacetic acid.

The hydrogen pressure that should be present during the reaction can be freely chosen by the person skilled in the art, depending on the speed of hydrogenation or possibly on the presence in the substrate to be hydrogenated of functional groups that are vulnerable to hydrogenation. The hydrogenation is preferably performed under hydrogen pressures of between 1 and 100 bar. Also preferred are pressures of between 5 and 15 bar, to ensure a correspondingly rapid hydrogenation.

The temperatures during hydrogenation should be in the range that appears normal to the person skilled in the art. A temperature of 10° C. to 150° C. is preferred. The process is most particularly preferably performed at between 30° C. and 80° C.

If enantiomer-concentrated substrates are used in the present process, the hydrogenation is very stereoconservative. The degree of racemisation is generally <10%, preferably <5%, more preferably <4% and most particularly preferably <3%. In an extremely preferred embodiment, the racemisation during the reaction can be <2% and even <1% and below.

The process provided by the invention is preferably performed in such a way that the compound to be hydrogenated is dissolved in the appropriate solvent, the catalyst is added and in a suitable apparatus the gas chamber, which has first been rendered inert, is supplied with hydrogen under a certain pressure. The stirred suspension is generally fully hydrogenated in 6 to 8 hours. The yields are close to 100% and the degree of racemisation, even with vulnerable substrates (phenylglycine) is less than 0.5%. It is precisely the combination of the possibility of being able to use expensive rhodium in tiny amounts, combined with the unexpectedly fast hydrogenation with optimum yields and enantiomer concentrations in the product, that puts these hydrogenation catalysts for the reaction according to the invention, which clearly stands out inventively from the prior art processes, in an exceptional position. Furthermore, the catalysts that are used can be recycled very effectively and reused in the reaction with no loss of activity. This also helps to save on operating costs, since on average less catalyst has to be used per quantity of substrate.

$(C_1-C_8)$ alkyl radicals should be understood to be methyl, ethyl, n-propyl, isopropyl, n-butyl, isobutyl, sec-butyl, tert-butyl, pentyl, hexyl, heptyl or octyl together with al their bond isomers. These can be substituted with one or more halogen, OH, $NH_2$, $NHR^2$ or $N(R^2)_2$ radicals.

The $(C_1-C_8)$ alkoxy radical corresponds to the $(C_1-C_8)$ alkyl radical, with the proviso that it is bonded to the molecule by an oxygen atom.

Radicals in which the alkyl chain is interrupted by at least one oxygen function, wherein two oxygen atoms cannot be connected to one another, are intended as $(C_2-C_8)$ alkoxyalkyl. The number of carbon atoms indicates the total number of carbon atoms contained in the radical.

$(C_3-C_8)$ cycloalkyl is understood to be cyclopropyl, cyclobutyl, cyclopentyl, cyclohexyl or cycloheptyl radicals, etc. These can be substituted with one or more halogens and/or radicals containing N, O, P, S, Si atoms and/or display N, O, P, S atoms in the ring, such as e.g. 1-, 2-, 3-, 4-piperidyl, 1-, 2-, 3-pyrrolidinyl, 2-, 3-tetrahydrofuryl, 2-, 3-, 4-morpholinyl.

A $(C_3-C_8)$ cycloalkyl $(C_1-C_8)$ alkyl radical denotes a cycloalkyl radical as described above, which is bonded to the molecule by an alkyl radical as specified above.

Within the meaning of the invention $(C_1-C_8)$ acyloxy denotes an alkyl radical as defined above having a maximum of 8 C atoms, which is bonded to the molecule by a COO function.

Within the meaning of the invention $(C_1-C_8)$ acyl denotes an alkyl radical as defined above having a maximum of 8 C atoms, which is bonded to the molecule by a CO function.

A $(C_6-C_{18})$ aryl radical is understood to be an aromatic radical having 6 to 18 C atoms. Examples include in particular compounds such as phenyl, naphthyl, anthryl, phenanthryl, biphenyl radicals or systems of the type described above which are annelated to the molecule concerned, such as e.g. indenyl systems, which can optionally be substituted with halogen, $(C_1-C_8)$ alkoxy, $(C_1-C_8)$ acyl, $(C_1-C_8)$ acyloxy.

A $(C_7-C_{19})$ aralkyl radical is a $(C_6-C_{18})$ aryl radical bonded to the molecule by a $(C_1-C_8)$ alkyl radical.

Within the meaning of the invention a $(C_3-C_{18})$ heteroaryl radical denotes a five-, six- or seven-membered aromatic ring system comprising 3 to 18 C atoms, which displays heteroatoms such as e.g. nitrogen, oxygen or sulfur in the ring. Such heteroaromatics are understood in particular to be radicals such as 1-, 2-, 3-furyl, such as 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl.

A $(C_4-C_{19})$ heteroaralkyl is understood to be a heteroaromatic system corresponding to the $(C_7-C_{19})$ aralkyl radical.

Suitable halogens are fluorine, chlorine, bromine and iodine.

The meaning of the expression "aromatic" or "heteroaromatic" is as understood by the general person skilled in the art. Definitions can be found e.g. in Bayer-Walter Lehrbuch der organischen Chemie, 1991, S. Hirzel Verlag, 22$^{nd}$ edition, p. 469ff. and p. 656 or p. 704ff.

Within the meaning of the invention, the term enantiomer-concentrated or enantiomer excess is understood to be the content of an enantiomer mixed with its optical antipode in a range from >50% to <100%. The ee value is calculated as follows:

([enantiomer1]−[enantiomer2])/([enantiomer1]+ [enantiomer2])=ee value

The structures shown relate to all possible diastereomers and in terms of a diastereomer to the possible two enantiomers of the compound in question that it encompasses (R or S; D or L).

EXPERIMENTAL EXAMPLES

Example 1

Production of D-cyclohexylglycine 100 g (661.5 mmol) D-phenylglycine are dissolved or suspended in 890 ml deionised water, 290 ml isopropanol and 66.7 ml (802 mmol) 37% hydrochloric acid. After addition of 10 g of the Pt/Rh catalyst, 4% Pt+1% Rh on activated carbon (water content approx. 50%, corresponding to approx. 5 wt. % catalyst relative to D-phenylglycine used), the reaction mixture is introduced into a 2 l hydrogenation autoclave. After being rendered inert with nitrogen three times, it is rinsed with hydrogen twice, then a hydrogen overpressure of 8-10 bar is established and the reaction solution heated to 50-60° C. After approximately 6 to 8 hours, hydrogen uptake is completed (theoretical amount of $H_2$ 44.4 l). The hydrogenator is depressurised and once again rendered inert with nitrogen three times. The still hot reaction solution is extracted with a nutsch filter and the catalyst is washed with 200 ml deionised water. The filtrate is first adjusted at 40-60° C. to a pH of 2-2.5 with 50% sodium hydroxide solution, during which process the first crystals form. It is then stirred for a further 15-30 minutes at this pH and then adjusted to a pH of 5-6 with 50% sodium hydroxide solution. The reaction mixture is cooled in an ice bath to a temperature of 0-10° C., the product is extracted with a nutsch filter, washed with 300 ml deionised water and dried in a drying oven in vacuo at 50-70° C.

The catalyst can be reused several times with no loss of activity.

Yield: 100-102 g (95.8-97.7%)

$^1$H-NMR (500 MHz, $D_2O$/NaOD): δ (ppm)=1-1.26 and 1.53-1.75 (each m, together 11H, cyclohexyl H), 3.02 (d, 1H, α-H)

In all the cases analysed, the enantiopurity of the D-cyclohexylglycine produced in this way (determined by GC with chiral separation phases) was identical to the enantiopurity of the D-phenylglycine used.

Example 2

Production of L-cyclohexylalanine 20 g (121 mmol) L-phenylalanine are dissolved or suspended in 200 ml deionised water, 200 ml isopropanol and 12.2 ml (146 mmol) 37% hydrochloric acid. After addition of 2 g of the Pt/Rh catalyst, 4% Pt+1% Rh on activated carbon (water content approx. 50%, corresponding to approx. 5 wt. % catalyst relative to L-phenylalanine used), the reaction mixture is introduced into a 1 l hydrogenation autoclave. After being rendered inert with nitrogen three times, it is rinsed with hydrogen twice, then a hydrogen overpressure of 8-10 bar is established and the reaction solution heated to 50-60° C. After approximately 6 to 8 hours, hydrogen uptake is completed (theoretical amount of $H_2$ 8.1 l). The hydrogenator is depressurised and once again rendered inert with nitrogen three times. The still hot reaction solution is extracted with a nutsch filter and the catalyst is washed with 50 ml deionised water. The filtrate is first concentrated to low volume in vacuo (the isopropanol largely removed), the residue then adjusted to a pH of 5-6 with 50% sodium hydroxide solution. It is cooled to a temperature of 0-10° C., the product is extracted with a nutsch filter, rinsed with 50 ml deionised water and dried in a drying oven in vacuo at 50-70° C.

Yield: 19.5 g (94.2%)

$^1$H-NMR (500 MHz, $D_2O$/NaOD): δ (ppm)=0.85-1.0 and 1.1-1.52 and 1.63-1.75 (each m, together 13H, cyclohexyl-H and cyclohexyl-$CH_2$), 3.3 (t, 1H, α-H)

Example 3

Production of (2R,1'RS)-3-(3'-piperidine) alanine×2 HCl (2R,1'RS)-2-amino-(3'-piperidine) propionic acid×2 HCl)

20 g (120 mmol) 3-(3'-pyridyl)-D-alanine are dissolved in 200 ml deionised water, 200 ml isopropanol and 12.2 ml (146 mmol) 37% hydrochloric acid. After addition of 2 g of the Pt/Rh catalyst, 4% Pt+1% Rh on activated carbon (water content approx. 50%, corresponding to approx. 5 wt. % catalyst relative to 3-(3'-pyridyl)-D-alanine used), the reaction mixture is introduced into a 2 l hydrogenation autoclave. After being rendered inert with nitrogen three times, it is rinsed with hydrogen twice, then a hydrogen overpressure of 8-10 bar is established and the reaction solution heated to 50-60° C. After approximately 4 hours, hydrogen uptake is completed (theoretical amount of $H_2$ 8.06 l). The hydrogenator is depressurised and once again rendered inert with nitrogen three times. The still hot reaction solution is extracted with a nutsch filter and the catalyst is washed with deionised water. The filtrate is evaporated in vacuo, 12 ml 37% HCl and 200 ml isopropanol are added, and it is evaporated again.

Yield: 29 g (98.6%), according to NMR a mixture of diastereoisomers (2R,1'S)- and (2R,1'R)-3-(3'-piperidine) alanine×2 HCl Example 4

Production of L-cyclohexylglycinol×HCl 27.4 g (200 mmol) L-phenylglycinol are dissolved in 220 ml 1 n hydrochloric acid and 200 ml isopropanol. After addition of 3 g of the Pt/Rh catalyst, 4% Pt+1% Rh on activated carbon (water content approx. 50%, corresponding to approx. 5.5 wt. % catalyst relative to L-phenylglycinol used), the reaction mixture is introduced into a 2 l hydrogenation autoclave. After being rendered inert with nitrogen three times, it is rinsed with hydrogen twice, then a hydrogen overpressure of 8-10 bar is established and the reaction solution heated to 50-60° C. After approximately 6 to 8 hours, hydrogen uptake is completed (theoretical amount of $H_2$ 13.4 l). The hydrogenator is depressurised and once again rendered inert with nitrogen three times. The still hot reaction solution is extracted with a nutsch filter and the catalyst is washed with deionised water. The filtrate is first largely concentrated to low volume in vacuo and the residue then taken up in 300 ml acetone and 100 ml MtBE added. It is cooled to a temperature of 0-10° C., the product extracted with a nutsch filter, rinsed with MtBE and dried in a drying oven in vacuo at 50° C.

Yield: 34.5 g (96.1%)

$^1$H-NMR (500 MHz, DMSO): δ (ppm)=0.95-1.2 and 1.55-1.75 (each m, together 11H, cyclohexyl-H), 2.8 (m, 1H, CH—N), 3.45-3.5 and 3.6-3.65 (each m, together 1H, $CH_2$—O), 5.25 (t, 1H, OH), 7.95 (s, 3H, $NH_3^+$)

What is claimed is:

1. A process for the hydrogenation of a compound, comprising hydrogenating a $C_6$-$C_{18}$ aromatic substituted amino acid or $C_6$-$C_{18}$ aromatic substituted amino alcohol in the presence of a platinum-rhodium mixed catalyst, wherein said $C_6$-$C_{18}$ aromatic substituted amino acid or $C_6$-$C_{18}$ aromatic substituted amino alcohol is of formula (I):

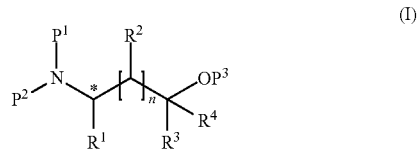

wherein n is 0, 1 or 2;

R$^1$ is a (C$_6$-C$_{18}$) aryl, or a (C$_7$-C$_{19}$) aralkyl, wherein aryl groups are optionally substituted with halogen, (C$_1$-C$_8$) alkoxy, (C$_1$-C$_8$) acyl, or (C$_1$-C$_8$) acyloxy;

R$^2$ is H, OH, (C$_1$-C$_8$) alkyl, (C$_2$-C$_8$) alkoxyalkyl;

R$^3$ and R$^4$ are each independently H, a (C$_1$-C$_8$) alkyl, a (C$_6$-C$_{18}$) aryl, or together denote an =O function;

P$^1$ and P$^2$ are each independently hydrogen, an amino protective group or together stand for a bifunctional amino protective group;

P$^3$ is hydrogen, a hydroxyl protective group, or a carboxyl protective group; and the carbon atom marked with * is an asymmetrical carbon atom;

and wherein;

said process produces a yield of greater than 94% after a reaction time of about 6 to 8 hours; and the hydrogenation reaction is performed in the presence of a solvent consisting of a mixture of water and an alcohol.

2. The process of claim 1, wherein n is 1 or 2.

3. The process of claim 2, wherein R$^3$ and R$^4$ are each independently a (C$_1$-C$_8$) alkyl, a (C$_6$-C$_{18}$) aryl, or together denote an =O function.

4. The process of claim 2, wherein R$^2$ is H, OH, (C$_1$-C$_8$) alkyl, (C$_2$-C$_8$) alkoxyalky.

5. The process of claim 1, wherein said platinum-rhodium mixed catalyst is used in a quantity of 0.1 to 20 wt %, relative to the compound undergoing hydrogenation and the ratio of platinum to rhodium in said platinum-rhodium mixed catalyst is between 20:1 and 1:1 (w/w).

6. The process of claim 1, wherein said platinum-rhodium mixed catalyst is adsorbed on a support.

7. The process of claim 1, wherein said hydrogenation is performed at a temperature of 10° C. to 150° C.

8. The process of claim 1, wherein said process comprises reacting said C$_6$-C$_{18}$ aromatic substituted amino acid or C$_6$-C$_{18}$ aromatic substituted amino alcohol with hydrogen gas in the presence of said platinum-rhodium mixed catalyst and under a hydrogen pressure of between 1 and 100 bar.

9. The process of claim 1, wherein:
a) R$^2$ is H;
b) R$^3$ and R$^4$ are H, or together denote an =O function; and
c) the ratio of platinum to rhodium in said platinum-rhodium mixed catalyst is between 20:1 and 1:1 (w/w).

10. The process of claim 9, wherein said platinum-rhodium mixed catalyst is used in a quantity of 0.1 to 20 wt %, relative to the compound undergoing hydrogenation.

11. The process of claim 10, wherein:
a) said hydrogenation is performed under a hydrogen pressure of between 1 and 100 bar; and
b) said hydrogenation is performed at a temperature of 10° C. to 150° C.

12. The process of claim 11, wherein said platinum-rhodium mixed catalyst is adsorbed on a support.

13. A process for the hydrogenation of a compound selected from the group consisting of: L-phenylalanine, D-phenylalanine, L-phenylglycine, D-phenylglycine, L-tyrosine or D-tyrosine, comprising hydrogenating said compound in the presence of a platinum-rhodium mixed catalyst wherein said process produces a yield of greater than 94% after a reaction time of about 6 to 8 hours, and wherein:
a) the hydrogenation reaction is performed in the presence of a solvent consisting of a mixture of water and an alcohol;
b) the ratio of platinum to rhodium in said platinum-rhodium mixed catalyst is between 20:1 and 1:1 (w/w);
said platinum-rhodium mixed catalyst is used in a quantity of 0.1 to 20 wt %, relative to the compound undergoing hydrogenation.

14. The process of claim 13, wherein said hydrogenation is performed at a temperature of 10° C. to 150° C.

15. The process of claim 14, wherein said process comprises reacting said compound with hydrogen gas in the presence of said platinum-rhodium mixed catalyst and under a hydrogen pressure of between 1 and 100 bar.

16. The process of claim 15, wherein said platinum-rhodium mixed catalyst is adsorbed on a support.

17. A process for the hydrogenation of a compound selected from the group consisting of: L-phenylalanine, D-phenylalanine, L-phenylglycine, D-phenylglycine, L-tyrosine or D-tyrosine, comprising hydrogenating said compound in the presence of a platinum-rhodium mixed catalyst wherein said process produces a yield of greater than 94% after a reaction time of about 6 to 8 hours, and wherein the hydrogenation reaction is performed in the presence of a solvent consisting of a mixture of water and an alcohol.

18. The process of claim 17, wherein the ratio of platinum to rhodium in said platinum-rhodium mixed catalyst is between 20:1 and 1:1 (w/w).

19. The process of claim 17, wherein said platinum-rhodium mixed catalyst is used in a quantity of 0.1 to 20 wt %, relative to the compound undergoing hydrogenation.

20. The process of claim 17, wherein said hydrogenation is performed at a temperature of 10° C. to 150° C. and under a hydrogen pressure of between 1 and 100 bar.

* * * * *